United States Patent [19]

Sato et al.

[11] Patent Number: 4,681,099
[45] Date of Patent: Jul. 21, 1987

[54] BREATH-SYNCHRONIZED CONCENTRATED-OXYGEN SUPPLIER

[75] Inventors: Toru Sato; Naoto Okazaki, both of Yonago; Katsumasa Fujii, Okayama, all of Japan

[73] Assignee: Tottori University, Tottori, Japan

[21] Appl. No.: 797,654

[22] Filed: Nov. 13, 1985

[30] Foreign Application Priority Data

Nov. 30, 1984 [JP] Japan ............................ 59-253495

[51] Int. Cl.$^4$ ............................................. A61M 16/00
[52] U.S. Cl. ............................ 128/204.23; 128/207.18
[58] Field of Search ....................... 128/204.21, 204.23, 128/204.26, 202.26, 205.12, 204.24, 203.14, 207.18

[56] References Cited

U.S. PATENT DOCUMENTS

| | | | |
|---|---|---|---|
| 3,357,428 | 12/1967 | Carlson | 128/204.23 |
| 4,281,651 | 8/1981 | Cox | 128/204.23 |
| 4,326,513 | 4/1982 | Schulz et al. | 128/204.23 |
| 4,331,455 | 5/1982 | Sato | 55/21 |
| 4,401,115 | 8/1983 | Monnier | 128/204.23 |
| 4,461,293 | 7/1984 | Chen | 128/204.23 |
| 4,534,346 | 8/1985 | Schlaechter | 128/205.12 |
| 4,584,996 | 4/1986 | Blum | 128/204.21 |
| 4,612,928 | 9/1986 | Tiep et al. | 128/204.23 |

*Primary Examiner*—Henry J. Recla
*Attorney, Agent, or Firm*—Spencer & Frank

[57] ABSTRACT

A breath-synchronized concentrated-oxygen supplier comprising an oxygen concentrator for producing and storing oxygen-enriched gas, and a buffer tank having an inlet connected to the oxygen concentrator and an outlet for temporarily storing the oxygen-enriched gas obtained from the concentrator. A valve is mounted in the outlet of the buffer tank so as to control flow of the oxygen-enriched gas from the buffer tank to the respiratory system of a living body, the valve having a gas flow path that is open to the atmosphere. A sensor, provided for sensing the respiration of the living body, generates an output signal indicative of the inhalation and exhalation phases of the respiration. An input device, on which a ratio between the entire length of the inhalation phase and a specific end portion thereof is set is included as is a regulator responsive to the sensor and input device for detecting the duration of each inhalation phase in succession based on the output signal from the sensor. The regulator also opens the valve at the beginning of each inhalation phase, and maintains the open time of the valve based on a period determined by a combination of averaging the preceding inhalation durations and the ratio set on the input device. Oxygen-enriched gas is supplied to the living body during each inhalation phase except for the specific end portion thereof, and the buffer tank acts to make the initial flow rate of the oxygen-enriched gas higher than the steady flow rate thereof in each inhalation phase.

4 Claims, 10 Drawing Figures

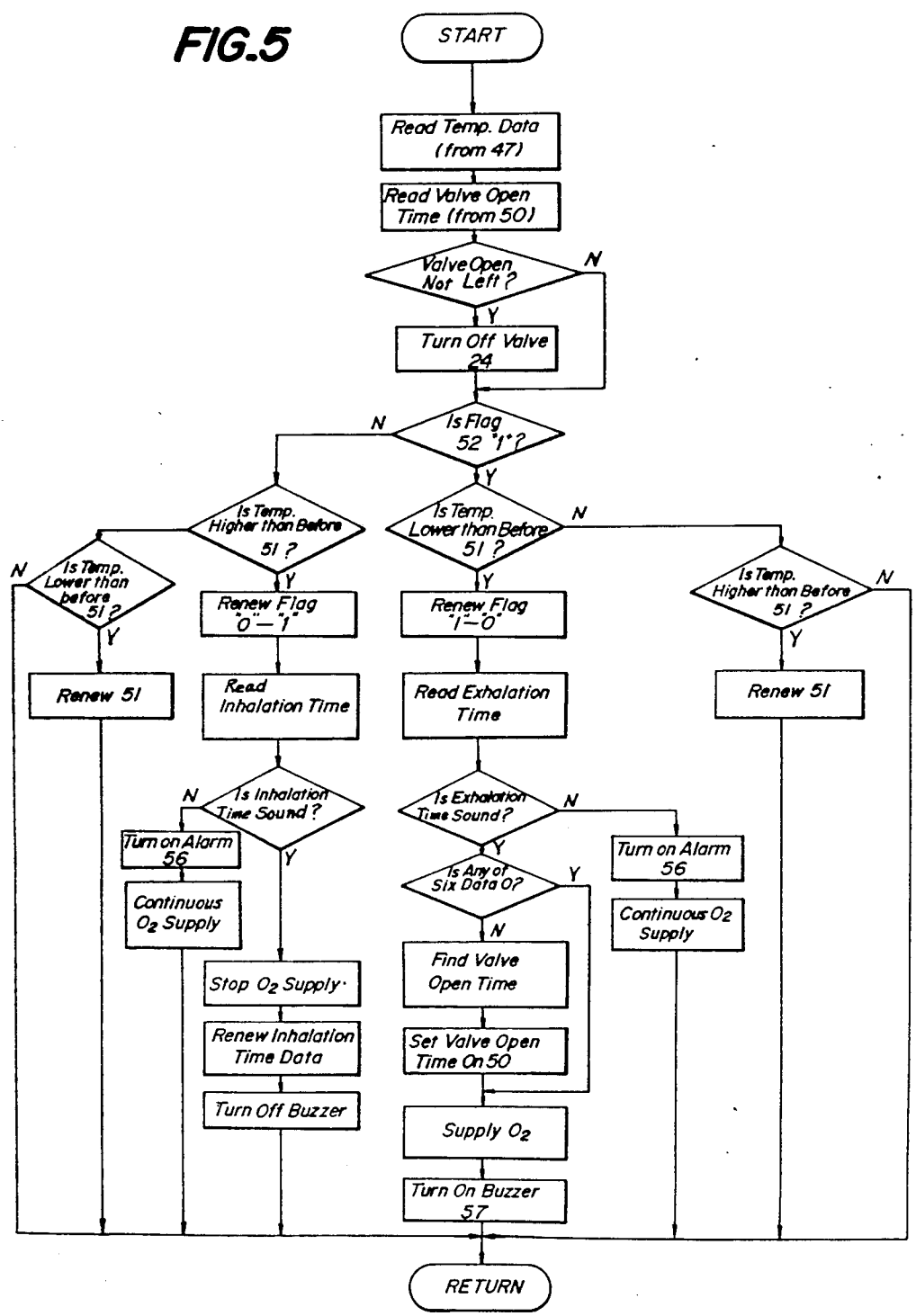

BREATH-SYNCHRONIZED CONCENTRATED-OXYGEN SUPPLIER

BACKGROUND OF THE INVENTION

1. Field of the Invention

This invention relates to a breath-synchronized concentrated-oxygen supplier, and more particularly to an apparatus which supplies oxygen-enriched gas to a patient in synchronism with the inhalation phase of his respiration.

2. Related Art Statement

With the recent progress in the medical art, an increasing number of oxygen concentrators have been used in inhalation therapy for patients suffering from respiratory ailment or circulatory diseases. Particularly, oxygen concentrators for home use have become remarkably popular these days, because they are capable of concentrating the oxygen gas in air by the use of a household electric power source through a simple operation, and supplying such concentrated oxygen gas for medical use. In the United States of America, a standard for the home oxygen concentrator, namely American National Standard Institute (ANSI) Z79. 13, 1981, has been established under the guidance of Federal Food and Drug Administration (FDA). Further, an international standard for it, e.g., International Organization for Standardization ISO 5059, is now ready to be published. In countries where medical treatment at home prevails, such oxygen concentrators are used to eliminate the inconvenience involved in the conventional oxygen distribution by use of heavy pressure vessels such as gas cylinders.

In general, there are two kinds of methods for treating patients by inhalation of oxygen gas or the like; namely, the so-called "closed circuit method" and the so-called "open circuit method".

The closed circuit method uses a "facemask apparatus" on the face or an endotracheal tube inserted into the trachea of the patient and supplies the gas to the patient through a passage, which is airtightly separated from the atmosphere and extends between the breathing device, i.e., the respirator or the gas supply system, and the patient's respiratory system. This closed circuit method has an advantage in its high inhaling efficiency, because the gas can be inhaled at about the same concentration as that of the gas supplied to the closed passage and the patient's breathing can be assisted or adjusted by regulating the pressure of the gas inside. However, the closed circuit method has a shortcoming in that it may cause irritation or discomfort on the side of the patient because of the covering of his mouth and nose and the direct insertion of a foreign substance in his trachea. Accordingly, the closed circuit method has been used mainly for seriously sick and unconscious patients or patients under anesthesia.

On the other hand, the open circuit method uses a breathing passage which is open to the atmosphere. In this method, the tip of the gas supplying tube is inserted into the nostril or the mouth of the patient so as to feed the gas without using any airtight connection between the apparatus and the face or upper airway of the patient, and the irritation or discomfort on the side of the patient are reduced and the patient is allowed to speak, eat or drink during the inhalation treatment by this method. Accordingly, this open circuit method is mainly used for mild cases in which self-breathing is possible.

In the closed circuit type breathing apparatus, oxygen or gas mixture for inhalation may be supplied in response to the patient's spontaneous breathing by detecting the gas pressure changes in the closed respiratory circuit, because the latter can be used as a triggering mechanism. However, in the conventional open circuit type breathing apparatus, it is difficult to detect a pressure change which is large enough to trigger the gas supply in the open respiratory circuit, and in most cases, the gas is supplied at a constant flow rate regardless of the patient's breathing. Accordingly, the gas is forced to the patient even during his exhalation and discomfort has been caused to the patient. Besides, a large part of the constantly fed gas is wasted because the gas supplied during patient's exhalation is discharged to the atmosphere without being used.

Besides, the open circuit type breathing apparatus is susceptible to undue dilution of oxygen concentration with air because it is open to the atmosphere. To cope with such partial pressure reduction of oxygen, it has been the practice to increase the flow rate of the constantly fed gas. However, the inventors have found that the transcutaneous tissue partial pressure of oxygen ($tcPO_2$) increases with the flow rate only up to 3 l/min, and the oxygenation in vivo hardly further increases even when the oxygen flow rate of insufflation exceeds the above value, as shown in Table 1.

TABLE 1

Transcutaneous Tissue Oxygen Partial Pressure for Different Constant Oxygen Flow Rates through a Nasal Cannula

| | Flow rate (l/min) | | | | |
|---|---|---|---|---|---|
| | 0.5 | 1.0 | 2.0 | 3.0 | 4.0 |
| Oxygen partial pressure (mmHg) | 89.9 ± 3.4 | 93.1 ± 4.5 | 129.7 ± 13.9 | 145.2 ± 5.8 | 151.0 ± 4.8 |

Thus, when the oxygen flow rate is excessively high in such an open circuit type breathing apparatus, a large amount of the oxygen gas will be wasted to the atmosphere without being used by the living body. Furthermore, with a high flow rate of oxygen, the stimulation to the patient becomes too strong and patient's discomfort increases. Accordingly, there is a limitation in the constant flow rate oxygen insufflation system in clinical practice.

To overcome the shortcomings of the conventional open circuit type breathing system, the Japanese Patent laid-open Publication No. 8,972/84 proposed a breath-synchronized open circuit type breathing system. In the breath-synchronized type, oxygen gas is supplied only during inhalations of the patient, so that this type breathing system has advantages in that the patient's comfort is ensured during the inhalation treatment and that the oxygen concentrator can be made small due to the reduced use of oxygen.

The oxygen concentrators can be classified into two types, i.e., the so-called membrane type and the so-called molecular adsorption type. The membrane type oxygen concentrator passes the air through a special membrane which transmits oxygen more easily than nitrogen, so that the oxygen concentration is enhanced by increasing the number of oxygen molecules relative to the number of nitrogen molecules. With this membrane type, the maximum attainable oxygen concentration is limited to about 40% at most. Thus, the membrane type concentrator is rather suitable for closed circuit type breathing system in which the oxygen gas is inhaled at about the same concentration as supplied by the oxygen concentrator.

In the molecular adsorption type (also referred to as "pressure swing adsorption" type), the air is passed through an adsorption cylinder filled with a special substance (adsorbent) while increasing and decreasing the air pressure, and nitrogen and moisture in the air are removed by repeated adsorption and desorption processes so as to produce highly concentrated oxygen. With this type concentrator, an oxygen concentration higher than 90% can be obtained. Thus, the molecular adsorption type concentrator is suitable for long inhalation treatments by using an open circuit type breathing system allowing the mixing of open air with the concentrated oxygen gas for inhalation.

However, the molecular adsorption type has a shortcoming in that when the outflow of the oxygen-enriched gas increases, the amount of purge gas for regenerating the adsorbent decreases, resulting in a gradual reduction of the oxygen concentration of the oxygen-enriched output gas. Such reduction of the oxygen concentration is contrary to the very purpose of the oxygen concentrator. As a countermeasure, it has been tried to use oxygen concentrators of larger size and to improve their technical performance, but there have been certain limits in such trial.

To solve such shortcoming of the molecular adsorption type oxygen concentrator, Japanese Patent Application Publication No. 5,571/82 corresponding to U.S. Pat. No. 4,331,455 proposes an oxygen concentrator using two adsorption cylinders, which cylinders are alternately operated in such a manner that during the adsorption cycle of one cylinder, a part of the oxygen-enriched output gas from that cylinder is used as the purge gas for the other cylinder. Such oxygen concentrator with the two adsorption cylinders has an advantage in that, even when adsorption cylinders of comparatively small capacity are used, oxygen-enriched gas with a desired concentration can be produced over a long period of time with a high stability because the two cylinders are efficiently purged with each other.

The respiration pattern of a human being or the like living body will be briefly reviewed now. The oxygen partial pressure in the arterial blood during respiration can be effectively increased by providing a sufficiently high peak flow rate of oxygen at the beginning of the inhalation phase. The inhaled gas at the end portion of the inhalation phase does not reach the respiratory organ but fills up the so-called dead space portion, so that it is not used effectively in the respiratory organ. In view of the above characteristics of the respiration pattern, the efficiency of the oxygen-enriched gas usage in terms of its utilization factor can be improved by using such breath-synchronized control in which a sufficiently high peak flow rate of oxygen-enriched gas is superposed onto the initial portion of the steady state flow rate of such gas during the inhalation phase while the oxygen-enriched gas supply is interrupted at a certain end portion of the inhalation phase.

The breath-synchronized open circuit type breathing system disclosed by the above-mentioned Japanese Patent Laying-open Publication No. 8,972/84, however, uses such control that a constant flow rate of the oxygen gas with a certain concentration is maintained during the inhalation phase and the interruption of the oxygen gas supply near the end of the inhalation phase is effected by a one-shot circuit which is actuated at the beginning of the inhalation phase, so that the oxygen is supplied for a predetermined period of time. Thus, with this breathing system, the oxygen partial pressure of the blood may not be raised so effectively and the utilization rate of the oxygen gas may not be sufficiently high. Further, the duration of oxygen gas supply for the inhalation phase is set at a certain value but is not variable in response to the patient's respiration, so that the breathing system cannot respond well to irregularity of the respiration and it may sometimes become out of synchronism with the patient's respiration, resulting in a still lower utilization rate.

The respiration pattern of a human being inherently varies from person to person, and even for one person, the speed and magnitude of the respiration vary depending on circumstances. Even under the same conditions, actual measurements of the durations of individual inhalations and exhalations show dispersions. Ideally, the timing and duration of the oxygen gas supply from the breathing system should be automatically controlled so as to be in synchronism with each of the ever varying inhalation timing and duration depending on the personal, circumstantial and individual respiratory differences.

The oxygen concentrator disclosed in the above-mentioned Japanese Patent Laying-open Publication No. 5,571/82 produces an almost constant flow rate of the oxygen gas with a certain concentration, so that it has shortcomings in that its utilization rate in terms of usage by the living body may be relatively low and that it may still cause irritation and discomfort on the side of patients or the like.

SUMMARY OF THE INVENTION

Therefore, an object of the invention is to obviate the above-mentioned difficulties of the prior art by providing a novel breath-synchronized concentrated-oxygen supplier which is capable of increasing the utilization factor of oxygen-enriched gas, minimizing the irritation, respiratory resistance and discomfort on the side of patient or the like living body, and reducing the size, weight and energy consumption of the supplier.

A preferred embodiment of the breath-synchronized concentrated-oxygen supplier according to the present invention uses an oxygen concentrator producing and storing oxygen-enriched gas, and a buffer tank which temporarily stores the oxygen-enriched gas from the oxygen concentrator. A valve is mounted on the outlet of the buffer tank so as to control the flow of the oxygen-enriched gas from the buffer tank toward the respiratory system of a living body through a path that is open to the atmosphere. Further, a suitable sensor is exposed to respiration of the living body, so as to generate an output signal indicative of inhalation (inspiratory) phase and exhalation (expiratory) phase of the respiration.

To interrupt the oxygen-enriched gas supply at a certain end portion of each inhalation phase, an input means is provided, so that the ratio between the entire length of the inhalation phase and a specific end portion thereof is set by an operator on the input means. The above valve is provided with such a regulator which is adapted to detect duration of each inhalation phase in succession based on the output signal from the sensor and, to open the valve at the beginning of each inhalation phase to keep the valve open for a period equivalent to the average of the preceding inhalation durations minus the portion corresponding to the above ratio set on the input means. Whereby, the oxygen-enriched gas is supplied to the living body during each inhalation phase except the above specific end portion thereof. The above buffer tank acts to make the initial flow rate of the oxygen-enriched gas higher than the steady state flow rate thereof in each inhalation phase.

In another embodiment of the invention, the above-mentioned oxygen concentrator is formed of a reservoir tank, at least two compressor-driven adsorption cylinders, and a controller adapted to run at least one of said adsorption cylinders at a time for producing the oxygen-enriched gas for storing in said reservoir while a portion of the oxygen-enriched gas thus produced is blown into remaining adsorption cylinders at rest for purging.

Each of the above compressor-driven adsorption cylinders may consist of an adsorption cylinder and a compressor directly connected thereto.

It is also possible to form the compressor-driven adsorption cylinders by connecting two or more adsorption cylinders to a common compressor through a selective valve. In the case of connecting two adsorption cylinders to one compressor, the selective valve may be a five-way valve adapted to connect one of said adsorption cylinders at a time to both said compressor and said exhaust passage.

In principle, the concentrated-oxygen supplier of the invention uses a combination of an oxygen concentrator and a breath-synchronizing means. To achieve the synchronism between the breath and the oxygen gas supply, the respiration of a living body is detected, for instance by disposing a temperature sensor, preferably a thermocouple, in front of the nostril and monitoring the change in the electromotive force of the thermocouple due to the temperature change of the respiratory air so as to find the inhalation phase by the temperature reduction during that phase, and a valve is opened in synchronism with the thus detected inhalation phase for starting the supply of the oxygen-enriched gas as the beginning of the inhalation phase.

Thus, the oxygen-enriched gas supply is interrupted during the exhalation phase, and this interruption causes the storing of the oxygen-enriched gas in a buffer tank at an elevated pressure. That elevated pressure facilitates the superposition of a pulse-like initial high flow rate onto the steady state flow rate of the oxygen-enriched gas when the above-mentioned valve is opened at the beginning of the inhalation phase. For each inhalation phase of the respiratory cycle, the duration in which the above valve is kept open is determined by a regulator based on a combination of the averaged duration of the preceding inhalation phases as determined by the output from the sensor and the ratio set on the input means from the outside. Thus, the oxygen-enriched gas supply is interrupted with such a timing that the oxygen-enriched gas is not supplied at that end portion of the inhalation phase in which the inhaled gas is filled in the dead space without being used.

BRIEF DESCRIPTION OF THE DRAWINGS

For a better understanding of the invention, reference is made to the accompanying drawings, in which:

FIG. 5 is a flow chart of the operation of the central processing unit CPU in the regulator of FIG. 3;

Throughout different views of the drawings, 1, 61 are oxygen concentrators, 2 is a reservoir tank, 3, 4 are absorption cylinders, 5, 7 are air cleaners, 6, 8 are compressors, 9, 10 are one-way valves, 11 is an orifice, 12, 13 are pressure switches, 14, 15 are solenoid-operated release valves, 16 is a silencer, 17 is a controller, 18 is a shutout solenoid valve, 19 is a reducing valve, 20 is a bacteria filter, 21 is a flow meter, 22 is a patient, 23 is a buffer tank, 24 is a breath-synchronizing solenoid valve, 25 is a humidifier, 26 is a nasal cannula, 27 is an oxygen analyzer, 28 is a thermocouple, 29 is a gas-supply regulator, 31, 32 are power source terminals, 33, 34, 35 are relays, 41 is a differential amplifier, 42, 43, 44 are operational amplifiers, 45 is a variable resistor, 46 is a low-pass filter, 47 is an A/D converter, 48 is an operational control unit, 49 is a central processing unit (CPU), 50 is a timer, 51, 52, 53, 54 are memories, 55 is an outside input means, 56 is an alarm, 57 is a buzzer, 62 is a five-way solenoid valve, 63 is a sliding valve, 64, 65 are passages, and 66 is a controller means.

DESCRIPTION OF THE PREFERRED EMBODIMENTS

Figure 1:
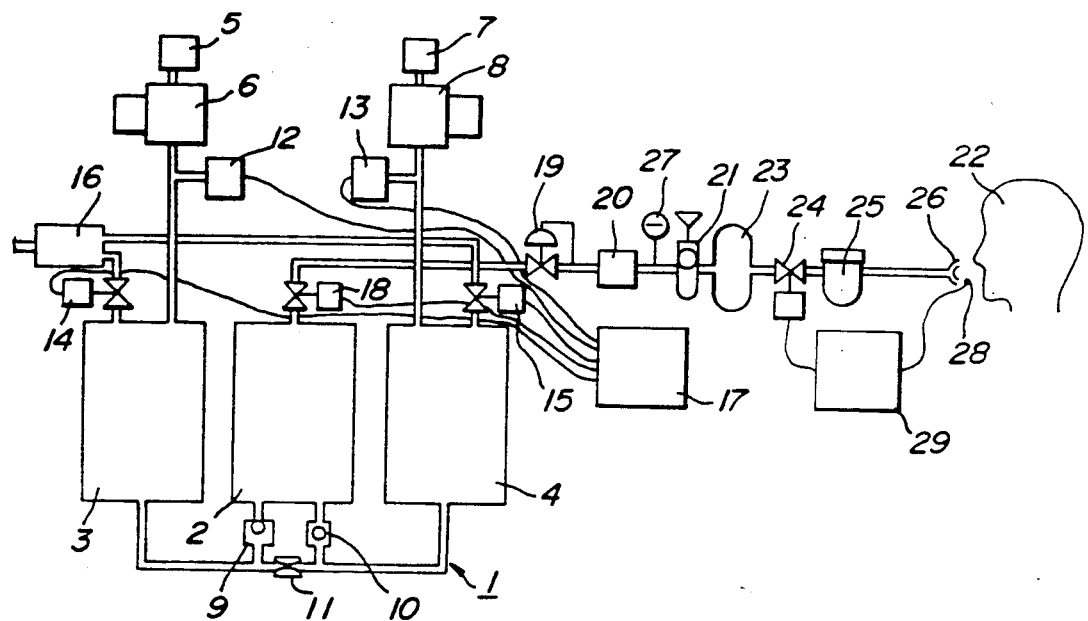
FIG. 1 is a diagrammatic illustration of a breath-synchronized concentrated-oxygen supplier according to the present invention.

Referring to FIG. 1 showing an enbodiment of the invention, an oxygen concentrator 1 consists of one reservoir tank 2 and two adsorption cylinders 3 and 4. The adsorption cylinder 3 is connected to a compressor 6 with an air cleaner 5, so that after being treated by the air cleaner 5 for dust removal the air is compressed by the compressor 6 and the compressed air is delivered to the adsorption cylinder 3. Similarly, the other adsorption cylinder 4 is connected to a compressor 8 with an air cleaner 7, so that compressed air from the compressor 8 is delivered to the adsorption cylinder 4. The adsorption cylinders 3 and 4 are connected to the reservoir tank 2 through one-way valves 9 and 10 respectively and the two cylinders 3 and 4 are also communicated to each other through an orifice 11, so that the oxygen-enriched gas produced by one adsorption cylinder 3 or 4 is fed to the reservoir tank 2 through the corresponding one-way valve 9 or 10 while a part of such gas is directed to the other adsorption cylinder 4 or 3 through the orifice 11 as purge gas.

Pressure switches 12 and 13 are mounted on the input side passages of the adsorption cylinders 3 and 4 respectively, while the input sides of the adsorption cylinders 3 and 4 are also connected to a common silencer 16 through solenoid-operated release valves 14 and 15 respectively. The output side of the silencer 16 is open to the atmosphere. A controller 17 is connected to the pressure switches 12, 13 and the release valves 14, 15. The controller 17 responds to signals from the pressure switches 12, 13 so as to control the operations of the compressors 6, 8, which are preferably of the linear motor type for generating oxygen-enriched gas therein in an alternate manner. The controller 17 also controls the release valves 14 and 15, so that substances separated from the adsorbent in the adsorption cylinders 3 or 4 by the purge gas are discharged to the atmosphere together with the purge gas through the release valves 14 or 15 and the silencer 16.

A shutout solenoid valve 18 is mounted on the output side passage of the reservoir tank 2. This valve 18 is closed when the concentrated oxygen supplier is at rest while it is kept open when the supplier is in operation, so that the oxygen-enriched gas is stored in the reservoir tank 2 during the rest period of the concentrated-oxygen supplier. Whereby, the reservoir tank 2 is kept ready for immediate operation when the supplier is restrarted. The pressure of the oxygen-enriched gas delivered through the shutout solenoid valve 18 is reduced to a proper level for inhalation treatment by a reducing valve 19, and the gas is purified by a bacteria filter 20 and its flow rate is adjusted at a level suitable for a patient 22 by a flow meter 21 having a needle valve type adjusting mechanism. The gas is then applied to a buffer tank 23, and a breath-synchronizing solenoid valve 24 controls the gas stream from the buffer tank 23 to a patient 22 through a humidifier 25 and a nasal cannula 16. The humidifier 25 gives a proper humidity to the oxygen-enriched gas so as to make it suitable for inhalation treatment of the patient 22.

An oxygen analyzer 27 may be provides at a suitable position the shutout solenoid valve 18 and the breath-synchronizing solenoid valve 24, so as to facilitate the detection of any malfunction of the oxygen concentrator 1, especially abnormality of the adsorbent, by operators such as medical doctors and nurses. In the illustrated embodiment, the oxygen analyzer 27 is provided between the bacteria filter 20 and the flow meter 21 as shown in FIG. 1.

As a sensor to detect the exhalation phase of the respiration of the patient 22, this embodiment uses a thermocouple 28 mounted on the nasal cannula 26 in such a manner that the thermocouple 28 is exposed to the respiratory air flow through the patient's nostril. The output from the thermocouple 28 is applied to a gas-supply regulator 29 which controls the operation of the breath-synchronizing solenoid valve 24 based on the information from the thermocouple 28.

Figure 2:
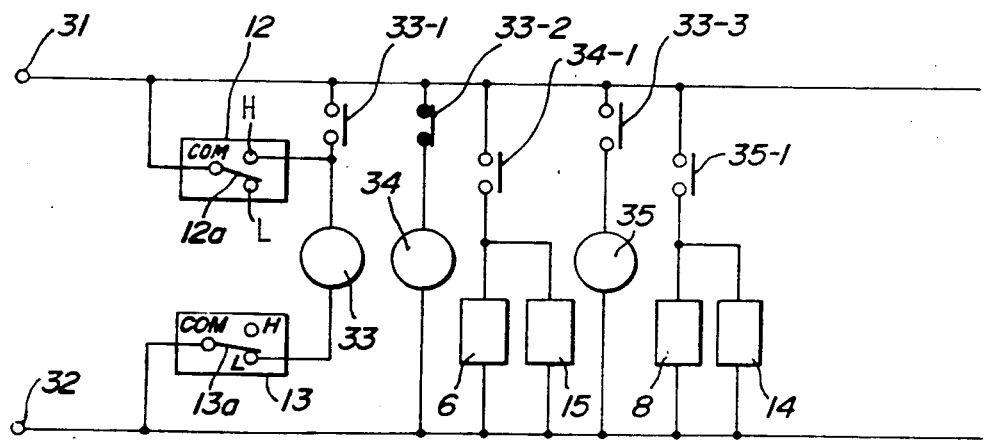
FIG. 2 is an electric circuit diagram showing a sequential control circuit for the controller of an oxygen concentrator in the concentrated-oxygen supplier of FIG. 1.

FIG. 2 shows a sequential circuit diagram of the controller 17 of FIG. 1. Each of the pressure switches 12 and 13 has three terminals; namely, a common contact COM connected to a fixed end of a swingable blade 12a or 13a, and two terminals H and L with with which the free end of the swingable blade 12a or 13a selectively comes in contact. In the illustrated embodiment, when the pressure in the corresponding adsorption cylinder 3 (4) is equal to or higher than a predetermined value, the swingable blade 12a (13a) is kept in contact with the terminal H, while the swingable blade 12a (13a) is kept in contact with the terminal L as long as the above pressure is below the above predetermined value. The terminal COM of the pressure switch 12 is connected to one power source terminal 31 while the terminal COM of the pressure switch 13 is connected to another power source terminal 32. The power source terminals 31 and 32 are connected to a suitable control power source not shown).

A relay 33 is provided between the terminal H of the pressure switch 12 and the terminal L of the other pressure switch 13. The relay 33 has two normally open relay contacts 33-1 and 33-3 and one normally closed relay contact 33-2. The normally open relay contact 33-1 is connected between the relay 33 and the power source terminal 31 as a self-hold contact for the relay 33. The normally closed relay contact 33-2 is serially connected to a relay 34, and the serial circuit of the relay contact 33-2 and the relay 34 is connected across the power source terminals 31 and 32. The normally open relay contact 33-3 is serially connected to a relay 35, and the serial circuit of the relay contact 33-3 and the relay 35 is also connected across the power source terminals 31 and 32.

The relay 34 has a normally open relay contact 34-1, which contact is connected between one power source terminal 31 and one junction of a parallel combination of the compressor 6 and the solenoid-operated release valve 15, the parallel combination having its opposite junction connected to the other power source terminal 32. The relay 35 has a normally open relay contact 35-1, which contact is connected between one power source terminal 31 and one junction of a parallel combination of the compressor 8 and the solenoid-operated release valve 14, the parallel combination having its opposite junction connected to the other power source terminal 32.

Figure 3:
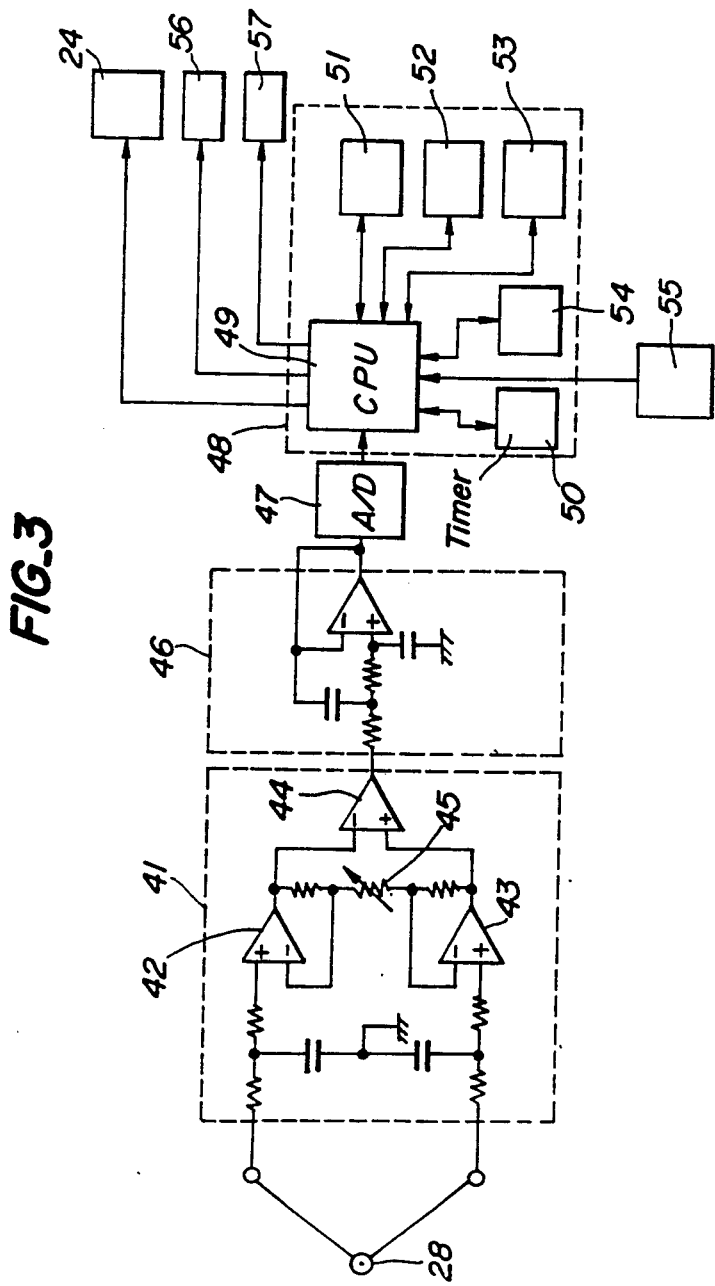
FIG. 3 is a block diagram of a regulator for controlling the gas supply through the supplier of FIG. 1.

FIG. 3 shows the electric circuit of the gas-supply regulator 29 of FIG. 1. The output from the thermocouple 28 acting as a sensor of respiration is applied to a differential amplifier 41 of the regulator 29. Operational amplifiers 42 and 43 of the differential amplifier 41 amplify the input from the thermocouple 28 and apply their output to an output stage operational amplifier 44 having a variable resistor 45 for gain adjustment. The output from the operational amplifier 44 is applied to a low-pass filter 46 for eliminating high-frequency noise and then converted into digital signals by an A/D converter 47, which digital signals are applied to an operational control unit 48. The control unit 48 has a central processing unit (CPU) 49, a timer 50, and memories 51 through 54. The CPU 49 is connected to an outside input means 55, such as a keyboard, through which means the ratio between the duration of an inhalation phase and the length of a specific end portion thereof is applied to the CPU 49 as input information.

Preferably, the gas-supply regulator 29 has a foolproof mechanism; namely, the above-mentioned ratio of a desired magnitude can be accepted only when it falls within a certain predetermined range, lest an extraneous input at the outside input means 55 by a mistake should cause a total stop of the oxygen-enriched gas supply.

The timer 50 has three functions; namely, a function of applying interruption signals to the CPU 49 for sampling the output from the A/D converter 47 at certain intervals, e.g., at every 10 msec in the illustrated embodiment, a function of measuring the open time of the breath-synchronizing solenoid valve 24 in the inhalation phase, and a function of measuring the duration of individual inhalation and exhalation phases. The memory 51 stores the data of preceding sampling, which sampling is effected in succession in a cyclic manner by the CPU 49. The memory 52 stores flags for identifying the inhalation phase and the exhalation phase, e.g., a bit "1" for the inhalation phase and a bit "0" for the exhalation phase as in the case of the illustrated embodiment. The memory 53 stores time data on inhalation phases of the immediately preceding six normal respiratory motions while updating them. The memory 54 stores a program for controlling the operational control unit 48.

The CPU 49 of the illustrated embodiment carries out the operations as instructed by the program from the memory 54 based on the data from the A/D converter 47, the time data on the past six normal inhalation phases as stored in the memory 53, and the data from the outside input means 55, so that control signals for the breath-synchronizing solenoid valve 24 are dispatched from the CPU 49 as a result of such operations. When an alarm 56 for indicating irregularity of the patient's respiration and a buzzer 57 for indicating the normal operation of the concentrated-oxygen supplier are provided, the CPU 49 also controls the operations of such alarm 56 and the buzzer 57.

The operation will be described now. The operation of the oxygen concentrator 1 will be explained at first by referring to FIG. 1 and FIG. 2. When the concentrator 1 is started without high pressure in the adsorption cylinders 3 and 4, the swingable blades 12a and 13a of the pressure switches 12 and 13 are kept on their L contacts, so that the relay 34 is energized. Accordingly, the normally open relay contact 34-1 is closed, and the compressor 6 is started and the solenoid-operated release valve 15 is actuated so as to open the passage from the adsorption cylinder 4 to the atmosphere through the silencer 16. Thus, the air purified by the air cleaner 5 and compressed by the compressor 6 is delivered into the adsorption cylinder 3, and nitrogen in the air thus delivered is adsorbed by the adsorbent filled in the cylinder 3 so as to increase the oxygen concentration of the air, and the oxygen-enriched gas from the cylinder 3 is stored in the reservoir tank 2 through the one-way valve 9.

At the same time, a part of the oxygen-enriched gas is delivered to the other adsorption cylinder 4 through the orifice 11 as the purge gas, so that nitrogen and moisture carried by the adsorbent in the cylinder 4 are released by the purge gas and discharged to the atmosphere through the now open release valve 15 and the silencer 16. Whereby, the ability of the adsorbent in the cylinder 4 is regenerated and revived.

In response to the operation of the compressor 6, the inside pressure of the adsorption cylinder 3 increases. When that inside pressure reaches a certain value, the swingable blade 12a of the pressure switch 12 is turned to the terminal H, so that the relay 33 is energized. Accordingly its normally open relay contact 33-1 is closed to complete the self-hold circuit of the relay 33, and the energization of the relay 33 is maintained by its own relay contact 33-1 even when the inside pressure of the adsorption cylinder 3 decreases and the swingable blade 12a of the pressure switch 12 is turned to the terminal L. Upon energization of the relay 33, its normally closed relay contact 33-2 is opened and its normally open relay contact 33-3 is closed, so that the relay 34 is de-energized and the relay 35 is energized. The de-energization of the relay 34 causes the relay contact 34-1 to open, and the compressor 6 comes to rest and the solenoid-operated release valve 15 is turned off and closed.

On the other hand, when the relay 35 is energized, its normally open relay contact 35-1 is closed, so as to start the compressor 8 and turn on the solenoid-operated release valve 14 for opening the passage from the adsorption cylinder 3 to the silencer 16. Thus, the gas in the adsorption cylinder 3 can be discharged to the atmosphere through the release valve 14 and the silencer 16, so as to facilitate the desorption of nitrogen and moisture adsorbed in the adsorbent in the cylinder 3. After the compressor 8 is started, the air cleansed by the air cleaner 7 and compressed by the compressor 8 is delivered through the adsorption cylinder 4 to the reservoir tank 2 as the oxygen-enriched gas through the one-way valve 10. A part of the oxygen-enriched gas from the cylinder 4 is also applied to the other cylinder 3 through the orifice 11 as the purge gas, so as to regenerate and reactivate the adsorbent in the cylinder 3 in the manner described above.

When the inside pressure of the adsorption cylinder 4 increases and reaches a certain value, the swingable blade 13a of the pressure switch 13 mounted on the input side of the adsorption cylinder 4 is turned to its terminal H, so as to de-energized the relay 33 in the circuit of FIG. 2. Hence, the relay 35 is de-energized and the relay 34 is energized again. Thus, the conditions of the control circuit of FIG. 2 come back to that at the beginning of the operation of the oxygen concentrator 1, and one cycle of the alternating operations of the adsorption cylinders 3 and 4 is completed. Thereafter, the above-described operation will be repeated in a cyclic manner, and the oxygen-enriched gas will be stored in the reservoir tank 2.

It is noted here that the oxygen concentrator 1 of the illustrated embodiment is adapted to ensure quick buildup of a sufficiently high oxygen concentration upon its start even if its preceding operation is ceased at an arbitrary time. More particularly, the actual control circuit of the oxygen 1 is such that even after the turning off of its start-stop switch, the above-described operation including the supply of the purge gas is maintained until the regeneration of the adsorbents in both of the adsorption cylinders 3 and 4 is completed, and upon completion of such regeneration, the operation is automatically brought to rest. Besides, in order to prevent the deterioration of the adsorbent due to its contact with the moisture of the open air when the oxygen concentrator 1 is not used, the adsorption cylinders 3 and 4 and the associated pipings in the embodiment of FIG. 1 are airtightly sealed from the air when the concentrator 1 is not used for any extended period of time.

Figures 4A, 4B:
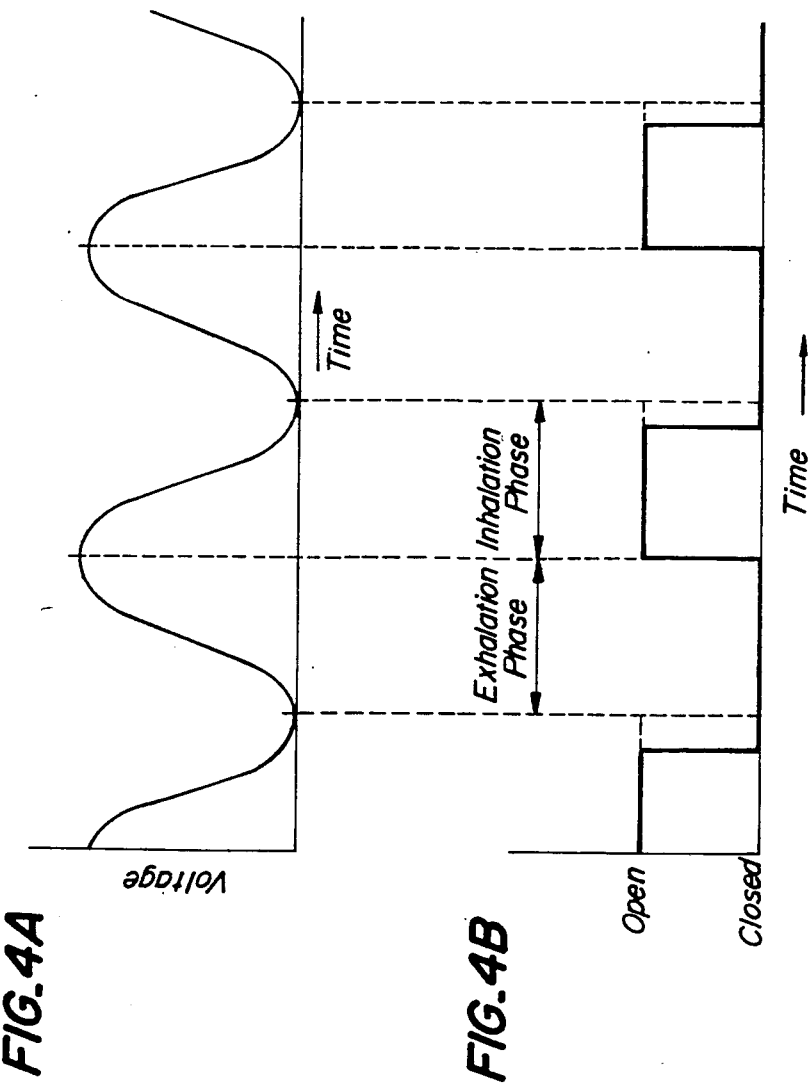
FIG. 4A and FIG. 4B are graphs which are used in the description of the operation of the supplier of FIG. 1.

The operation of the gas-supply regulator 29 will be described now. FIG. 4A shows the waveform of the output voltage from the thermocouple 28 as seen at the input side of the A/D converter 47 after the amplification at the differential amplifier 41 and the noise elimination at the low-pass filter 46. Since the thermocouple 28 is exposed to the respiratory air passing the patient's nostril, its output voltage gradually increases during the exhalation phase in which the air is exhaled from the inside of the patient's body while its output gradually decreases during the inhalation phase. Thus, the output voltage of the thermocouple 28 is approximately sinusoidal.

The A/D converter 47 converts the output of the thermocouple 28 into digital signals in the following manner. The CPU 49 samples the voltage of FIG. 4A at a regular interval of 10 msec in response to the interruption signal from the timer 50 and the sampled value is stored in the memory 51 as a temperature datum, and the CPU 49 compares the latest temperature as sampled against the preceding temperature datum retrieved from the memory 51. If the latest temperature as sampled is higher than the preceding temperature datum, the respiration is in the exhalation phase wherein the output voltage of the thermocouple 28 gradually increases as shown in FIG. 4A. On the other hand, if the latest temperature as sampled is lower than the preceding temperature datum, the respiration is in the inhalation phase wherein the output voltage of the thermocouple 28 gradually decreases as also shown in FIG. 4A. To identify the durations of the exhalation and inhalation phases, a binary flag "1" for exhalation and a binary flag "0" for inhalation are stored in the memory 52 during the respective phases.

Let it be assumed that, at a certain instant, the memory 52 carries a binary flag "1" indicating that the respiration is in the exhalation phase. During the exhalation phase, the temperature datum stored in the memory 51 is renewed by the latest sampled temperature only when such latest temperature as sampled from the A/D converter 47 is higher than the preceding temperature datum retrieved from the memory 51. If the latest temperature as sampled is lower than the preceding temperature datum retrieved from the memory 51, i.e., at the transit from the exhalation phase to the inhalation phase, the binary flag in the memory 52 is changed to "0" and the latest lower temperature as sampled is stored in the memory 51 as a new datum. At the same time, the breath-synchronizing solenoid valve 24 is turned on for opening the passage to the nasal cannula 26, and the supply of oxygen-enriched gas to the patient 22 starts while the buzzer 57 starts to sound. Thereafter, during the inhalation phase, as long as the newly sampled temperature is lower than the preceding temperature datum, such newly sampled temperature is stored in the memory 51 for renewing the temperature datum therein.

Both the duration of the inhalation phase from the exhalation-inhalation transit to the inhalation-exhalation transit and the duration of the exhalation phase from the inhalation-exhalation transit to the exhalation-inhalation transit are measured by a combination of the CPU 49 and the timer 50. Whether each of the thus measured duration falls in a normal range or not is checked by a program stored in the memory 54. In the illustrated embodiment, the normal range of the duration of both the inhalation and exhalation phases is assumed to be 1–15 seconds. When the durations of the inhalation and exhalation phases are normal, data on the immediately preceding six consecutive sound inhalation durations are stored in the memory 53 while renewing them in succession.

On the other hand, if any of the inhalation durations and exhalation durations falls outside the above normal range, it is assumed that an abnormality of a kind has occurred on the side of the patient 22 or the thermocouple 28. Such abnormality is communicated to the doctors and nurses by actuating the alarm 56 by the CPU 49. At the same time, the breath-synchronizing solenoid valve 24 is controlled in such a manner that the oxygen-enriched gas is continuously supplied to the patient 22. The renewal of the data on the preceding six consecutive sound inhalation durations is effected when a new inhalation duration datum of the latest sound respiratory cycle is made available by erasing the oldest (seven respiratory cycles before) datum and storing such new inhalation duration datum.

When the respiratory cycles are sound, the oxygen-enriched gas is supplied only in the inhalation phase. The duration of such supply, namely, the duration of the opening of the breath-synchronizing solenoid valve 24 (to be referred to as the "valve open time"), is controlled by a combination of a time ratio set on the outside input means 55 and the average of the preceding six consecutive sound inhalation durations. More particularly, at the transit from the exhalation phase to the inhalation phase, data on the immediately preceding six consecutive sound inhalation durations are read from the memory 53 for determining the average value thereof. The product of that average value of the inhalation durations and the time ratio set on the outside input means 55 is calculated. The valve open time is determined by subtracting the above product from the above average value of the six inhalation durations.

That valve open time is set on the timer 50, and as the oxygen-enriched gas is supplied it is counted down, so that when the thus set time is reduced to zero by the counting down the breath-synchronizing solenoid valve 24 is closed. Thus, the valve open time for the breath-synchronizing solenoid valve 24 for a specific inhalation phase is shorter than the average value of the immediately preceding six consecutive inhalation durations by the time ratio set on the outside input means 55, as shown in FIG. 4B. The gas to be filled in the trachea or other dead space of the patient 22 is provided by the atmospheric air inhaled by him during the time corresponding to the above time ratio.

If the actual duration of an inhalation phase is shorter than the valve open time set on the timer 50 for that inhalation phase, the CPU detects the transit from the inhalation to exhalation based on the temperature data during the above counting down at the timer 50, and the flag in the memory 52 is changed from "0" to "1". Thus, in this case the breath-synchronizing solenoid valve 24 is closed before the valve open time is counted to zero at the timer 50.

FIG. 5 shows a flow chart of the operation of the CPU 49 in response to the interruption signals from the timer 50 at 10 msec intervals. The operation of the CPU will be summarized now. When the operation of the gas-supply regulator 29 is started, the temperature variation of the respiratory air of the patient or the like living body is monitored as a pattern. In this embodiment, the breath-synchronizing solenoid valve 24 is kept open at first until six consecutive sound inhalation duration data are stored in the memory 53, so that the oxygen-enriched gas is continuously supplied to the patient's respiratory organ during such initial period. In each inhalation phase after data on the six consecutive sound inhalation durations are stored in the memory 53, the valve open time for that inhalation phase is determined based on the average of the thus stored data in the memory 53 and the time ratio set on the outside input means 55, and the breath-synchronizing solenoid valve 24 is turned on from the start of that inhalation phase for the period of the thus determined valve open time so as to supply the oxygen-enriched gas to the respiratory organ of the patient 22 or the like living body.

As long as the sound respiratory pattern is maintained, the inhalation duration data older than six respiratory cycles before the present instant are erased from the memory 53, so as to ensure the derivation of the average of the latest six consecutive sound inhalation durations. When the duration of inhalation or exhalation phase falls outside of a normal duration range (to be separately set), the breath-synchronizing solenoid valve 24 is immediately turned on so as to continuously supply the oxygen-enriched gas to the patient or the like, and at the same time the alarm 56 is actuated. When the sound respiration is resumed thereafter and conditions for normal operation are met, the breath-synchronized operation is resumed and the alarm 56 is turned off. However, unless the sound respiration is resumed, the continuous supply of the oxygen-enriched gas is maintained and the alarm 56 is continuosly actuated.

In the above example, the valve open time of the breath-synchronizing solenoid valve 24 is determined based on the preceding six consecutive inhalation durations. However, the invention is not restricted to such preceding six inhalation durations, and an average of an arbitrary number of the preceding inhalation durations can be used for determining the valve open time. As another modification, the valve open time may be determined by taking the product of the duration of the immediately preceding inhalation phase and the time ratio set on the outside input means 55 and by subtracting such product from the duration of the immediately preceding inhalation phase. Further, the valve open time for a following inhalation phase may be determined by taking the average of such a calculated time determined based on the immediately preceding inhalation duration and more preceding valve open times. That is, the valve open time for the next inhalation phase is determined by an average of the preceding valve open time and the present inhalation duration so measured minus a product of it and the ratio set on the outside input means.

Figure 6:
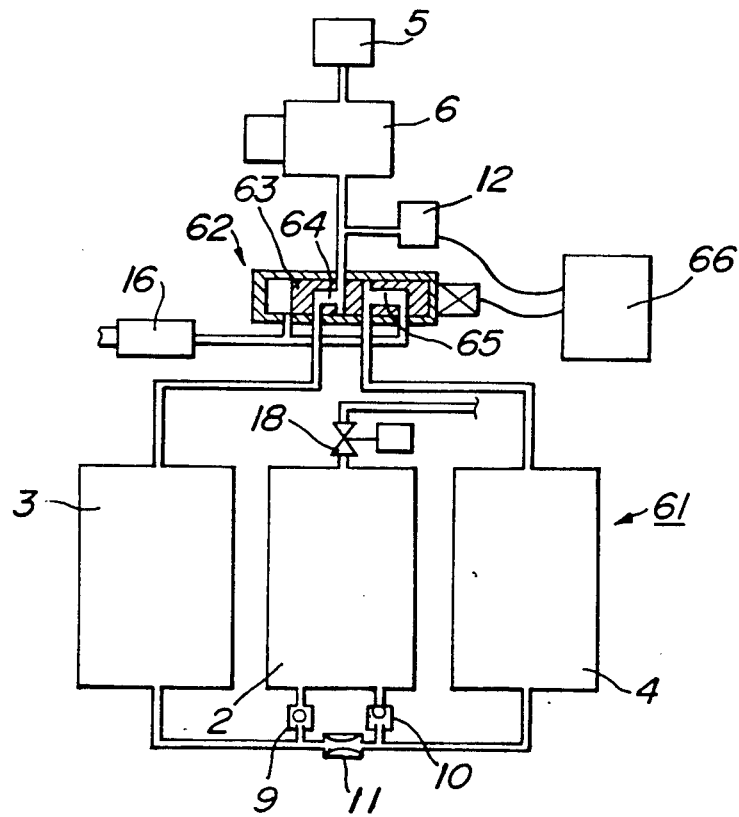
FIG. 6 is a block diagram of another oxygen concentrator which can be used in the supplier of the invention.

FIG. 6 shows another embodiment of the oxygen concentrator to be used in the concentrated-oxygen supplier of the invention. The oxygen concentrator 61 of this embodiment uses one compressor 6 which is alternately connected to two adsorption cylinders 3 and 4 through a five-way solenoid valve 62. The formation of the oxygen concentrator 61 is similar to that of the oxygen concentrator 1 of FIG. 1 except for the above five-way solenoid valve 62 and the use of only one compressor 6. Like parts are designated by like numerals. The five-way solenoid valve 62 has a sliding valve 63 which can selectively assume a first position as shown in FIG. 6 and a second position to the left thereof. At the first position, the valve 63 connects the compressor 6 to the adsorption cylinder 3 through a passage 64 while connecting the adsorption cylinder 4 to the silencer 16 through another passage 65. The valve 63 located at the second position connects the compressor 6 to the adsorption cylinder 4 through the passage 65 while connecting the adsorption cylinder 3 to the silencer 16 through the passage 64.

A controller means 66 shifts the valve 63 between the first position and the second position in response to the output from the pressure switch 12. More particularly, when the compressor 6 operates with the valve 63 at the position 1 as shown in FIG. 6, the air cleansed by the air cleaner 5 and compressed by the compressor 6 enters the adsorption cylinder 3 through the passage 64, so as to produce oxygen-enriched gas. As in the case of FIG. 1, the thus produced oxygen-enriched gas is stored in the reservoir tank 2 through the one-way valve 9, and at the same time a part of the oxygen-enriched gas is delivered to the other adsorption cylinder 4 through the orifice 11 as purge gas. The purge gas causes desorption of nitrogen and moisture from the adsorbent in the adsorption cylinder 4, and the desorption products are discharged to the atmosphere together with the purge gas through the passage 65 and the silencer 16.

When the inside pressure of the adsorption cylinder 3 increases and reaches a certain predetermined value, the pressure switch 12 generates and transmits such a signal to the controller means 66 that the sliding valve 63 is shifted from the position 1 to the left as seen in FIG. 6 until reaching its second position. Whereby, the gas in the adsorption cylinder 3 is discharged to the atmosphere together with desorbed nitrogen and moisture through the passage 64 and the silencer 16. At the same time, the air cleansed by the air cleaner 5 and compressed by the compressor 6 enters the adsorption cylinder 4 through the passage 65 for producing the oxygen-enriched gas. The thus produced oxygen-enriched gas is stored in the reservoir tank 2 through the one-way valve 10, while a part of the oxygen-enriched gas is delivered to the adsorption cylinder 3 through the orifice 11 as the purge gas for effecting the regeneration and reactivation of the adsorbent therein.

Thereafter, when the inside pressure of the adsorption cylinder 4 increases and reaches the above-mentioned certain predetermined value, the controller means 66 shifts the valve 63 of the five-way valve 62 to the first position as shown in FIG. 6. Whereby, the oxygen concentrator comes back to the initial condition and one cycle of the operation of the oxygen concentrator of FIG. 6 is completed.

Accordingly, when the five-way valve 62 is used, one compressor 6 can alternatively pressurize and purge the two adsorption cylinders as in the case of FIG. 1 using two compressors. It should be noted that the oxygen concentrator to be used in the concentrated-oxygen supplier of the invention is not restricted to the above adsorption type, and membrane type oxygen concentrator can also be used in the present invention.

As described in the foregoing, the breath-synchronized concentrated-oxygen supplier of the invention uses a combination of an oxygen concentrator, a buffer tank, a breath-synchronizing solenoid valve, and a gas-supply regulator which limits the opening time of the above solenoid valve only to a period available for useful usage of the oxygen gas, so that the following outstanding effects can be achieved.

(a) Table 2 shows the result of tests on the change of oxygen concentration of the oxygen-enriched gas in breathing apparatuses for two cases both using the same adsorption type oxygen concentrator; namely, a case of the breath-synchronzed type of the invention and another case of a conventional continuous type.

TABLE 2

| | Oxygen Concentration and Supply Method | |
|---|---|---|
| | Oxygen Concentration (%) | |
| Flow Rate (l/min) | Continuous supply | Breath-synchronized supply |
| 1 | 94 | 94 |
| 2 | 90 | 94 |
| 3 | 76 | 90 |
| 4 | 58 | 86 |
| 5 | 50 | 80 |

As can be seen from Table 2, the breath-synchronized type supply according to the invention, which supplies the oxygen gas only during the inhalation phase, improves the performance and inhalation efficiency of the supplier to a great extend in comparison with the conventional continuous supply type. If breathing apparatuses of the breath-synchronized supply type and the continuous supply type are made to obtain the same inhalation efficiency by using the same oxygen concentrator, the breath-synchronized supply type can be made much smaller in size, lighter in weight, and more energy saving than the continuous supply type. Accordingly, the concentrated-oxygen supplier of the invention makes an epoch-making progress in the art and makes the oxygen inhalation treatment at home more readily available.

Figure 7A:
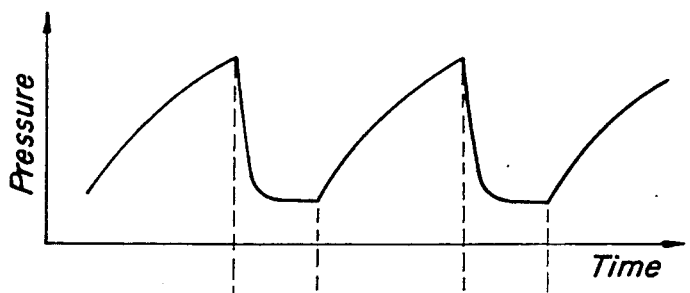
FIG. 7A, FIG. 7B and FIG. 7C are graphs illustrating the effects produced by the invention.
Figure 7B:
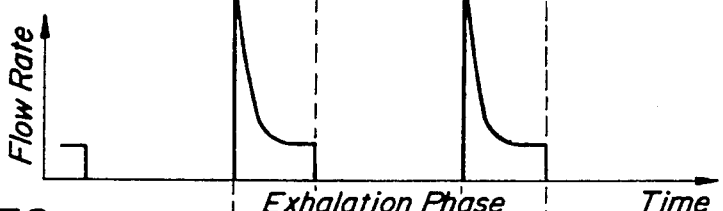
Figure 7C:
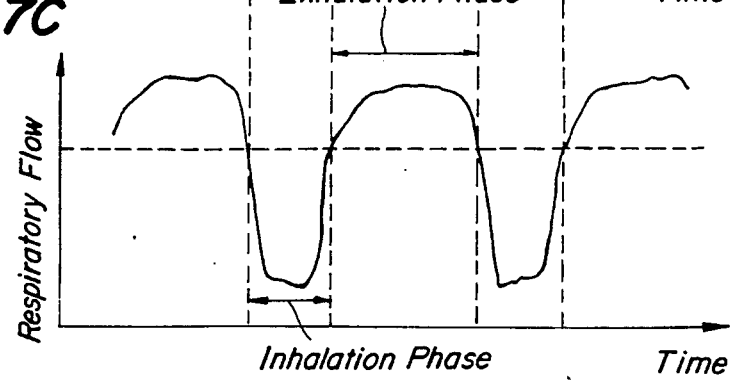

(b) A buffer tank is provided upstream of the breath-synchronizing solenoid valve, so that the pressure in the buffer tank is raised during the exhalation phase wherein the supply of oxygen-enriched gas is halted, as shown in FIG. 7A. The discharge of such raised pressure at the beginning of the inhalation phase results in a sufficiently high peak-like initial flow rate of the oxygen-enriched gas which is superposed on the steady flow rate in each inhalation phase, as shown in FIG. 7B. Such peak-like initial high flow rate matches the steep change in the respiratory flow curve from the end of the exhalation phase to the very beginning of the inhalation phase in the respiration of the living body, as shown in FIG. 7C. Thus, the superposition of the above initial peak of the oxygen flow rate suits the respiratory pattern of the living body very well.

Oxygen inhalation efficiency in the living body was tested with four models of inhalation; namely, a model (1) with inhalation of air, a model (2) with a continuous supply of oxygen-enriched gas at 2 l/min from an oxygen concentrator, a model (3) with a supply of oxygen-enriched gas at 2 l/min only for inhalation phases from an oxygen concentrator through a three-way valve which discharged the oxygen-enriched gas to the atmosphere during exhalation phases, and a model (4) with a supply of oxygen-enriched gas at 2 l/min only for inhalation phases from an oxygen concentrator through a two-way valve which stored the oxygen-enriched gas in a buffer tank during exhalation phases. The result is shown in Table 3.

TABLE 3

Transcutaneous Tissue Oxygen Partial Pressure in Living Body for Different Inhaling Models

| Model | Transcutaneous Tissue O$_2$ Partial Pressure (tcPO$_2$) (mmHg) |
| --- | --- |
| (1) | 73.1 ± 5.4 |
| (2) | 122.7 ± 10.5 |
| (3) | 105.5 ± 15.3 |
| (4) | 163.1 ± 12.6 |

Similarly, oxygen inhalation efficiency in the living body was tested for different flow rates of inhaling oxygen gas under different gas supplying conditions; manely, condition (i) under continuous oxygen gas supply, condition (ii) under intermittent oxygen gas supply with a 100 ml buffer tank, condition (iii) under intermittent oxygen gas supply with a 200 ml buffer tank, and condition (iv) under intermittent oxygen gas supply with a 400 ml buffer tank. The result is shown in Table 4.

TABLE 4

Transcutaneous Oxygen Partial Pressure in Living Body for Different Gas Supply Rates Transcutaneous Tissue O$_2$ Partial Pressure (tcPO$_2$) (mmHg)

| Supply Conditions | Oxygen Flow Rate (l/min) | | | |
| --- | --- | --- | --- | --- |
|  | 0.5 | 1.0 | 2.0 | 3.0 |
| (i) | 89.9 ± 3.4 | 93.1 ± 4.5 | 129.7 ± 13.9 | 145.2 ± 5.8 |
| (ii) | 101.3 ± 4.6 | 109.7 ± 6.5 | 173.4 ± 18.1 | 193.9 ± 17.5 |
| (iii) | 101.8 ± 3.5 | 112.5 ± 12.3 | 175.2 ± 18.6 | 191.7 ± 15.6 |
| (iv) | 102.6 ± 3.1 | 108.4 ± 4.0 | 173.1 ± 12.2 | 191.1 ± 20.8 |

As can be seen from the test results of Table 3 and Table 4, with the intermittent supply of oxygen, the oxygen-enriched gas can be inhaled at a very high efficiency. Especially, the model (4) of Table 3 shows that the use of the buffer tank, the capacity of which as small as 100 ml is shown to be effective enough in Table 4, improves the effectiveness of the breath-synchronized concentrated-oxygen supply system to a greater extent.

(c) Since the duration of the supply of the oxygen-enriched gas for each inhalation phase is controlled by a combination of the preceding inhalation durations and the time ratio of a specific end portion of the inhalation duration as set through an outside input means, and oxygen-enriched gas can be supplied in excellent synchronism with the respiration of the patient or the like, so that the efficiency of the oxygen gas supply can be further improved. In view of the high inhalation efficiency thanks to the use of the buffer tank, the time ratio indicating the length of the specific end portion of the inhalation duration, in which end portion the gas supply is interrupted, can be made comparatively large.

Thus, the invention facilitates further miniaturation, weight reduction and energy saving in the oxygen concentrator.

(d) The oxygen concentrator in the illustrated embodiment of the invention uses two adsorption cylinders which are operated alternately in such a manner that a part of the oxygen-enriched gas produced by one adsorption cylinder and saved by closing the breath-synchronizing valve is delivered to the other adsorption cylinder as purge gas, so that the oxygen concentrator can operate at a fairly high flow rate of the oxygen-enriched gas without reducing the oxygen concentration therein. Accordingly, the performance of such oxygen concentrator can be considerably improved as compared with conventional oxygen concentrators. The improved performance facilitates further miniaturation, weight reduction and energy saving in the oxygen concentrator.

The interruption of the supply of the oxygen-enriched gas during exhalation phases contributes to speeding up of the pressure buildup at the adsorption cylinders and quickening of the switching of the alternate operations of the adsorption cylinders. The effect of such quickened switching will be positively combined with the above-mentioned effect of the alternate operation of two adsorption cylinders in improving the performance of the oxygen concentrator.

(f) The thermocouple used in the above embodiment for sensing the patient's respiration produces signals which accurately follow the respiration and facilitates accurate control. The thermocouple as the respiration sensor can be made small and light so as to eliminate the resistance to respiration and to reduce the patient's uneasy feeling, and such sensor with stable performance can be manufactured at a low cost on a mass production basis. In fact, it may be discarded after each inhalation treatment.

(g) The buzzer used in the above embodiment sounds in synchronism with the operation of the break-synchronizing solenoid valve, so as to inform the patient of the orderly operation of the breathing apparatus. Whereby, the patient becomes confident with the reliable operation of the apparatus. Besides, such buzzer can be used for training the patient in learning a proper respiratory rhythm suitable to him, which training is useful in rehabilitation from a chronic respiratory ailment.

(h) When a membrane type oxygen concentrator is used, the service life of the selectively permeable membrane therein can be improved by minimizing the oxygen production through suppression of the wasteful use of oxygen.

Although the invention has been described with a certain degree of particularity, it is understood that the present disclosure has been made only by way of example and that numerous changes in details of construction and the combination and arrangement of parts may be resorted to without departing from the scope of the invention as hereinafter claimed.

What is claimed is:

1. A breath-synchronized concentrated-oxygen supplier, comprising
    an oxygen concentrator producing and storing oxygen-enriched gas;
    a buffer tank having an inlet connected to said oxygen concentrator and an outlet, said buffer tank temporarily storing the oxygen-enriched gas from the oxygen concentrator;
    a valve mounted in said outlet of said buffer tank so as to control flow of the oxygen-enriched gas from the buffer tank, patient connection means connected to said outlet and adapted to be connected to a respiratory system of a living body and having a gas flow path that is open to the atmosphere;
    sensor means for sensing the respiration of the living body and adapted to generate an output signal indicative of the inhalation phase and the exhalation phase of the respiration;
    an input means on which a ratio between the entire length of the inhalation phase and a specific end portion thereof is set; and
    regulator means responsive to said sensor means and input means and adapted to detect the duration of each inhalation phase in succession based on the output signal from said sensor means and to open said valve at the beginning of each inhalation phase, as well as to maintain the open time of said valve based on a period determined by a combination of averaging the preceding inhalation phase durations and said ratio set on the input means; whereby oxygen-enriched gas is supplied to said living body during each inhalation phase except said specific end portion thereof, and said buffer tank acts to make the initial flow rate of the oxygen-enriched gas higher than the steady flow rate thereof in each inhalation phase.

2. A breath-synchronized concentrated-oxygen supplier as set forth in claim 1, wherein said oxygen concentrator has a reservoir tank, at least two compressor-driven adsorption cylinders, and a controller adapted to run at least one of said adsorption cylinders at a time for producing the oxygen-enriched gas for storing in said reservoir while a portion of the oxygen-enriched gas thus produced is blown into the remaining adsorption cylinders at rest for purging.

3. A breath-synchronized concentrated-oxygen supplier as set forth in claim 2, wherein each of said compressor-driven adsorption cylinders has an adsorption cylinder and a compressor directly connected thereto.

4. A breath-synchronized concentrated-oxygen supplier as set forth in claim 2, wherein said compressor-driven adsorption cylinders consist of one compressor, one exhaust passage, two adsorption cylinders, and a five-way valve adapted to connect one of said adsorption cylinders at a time to both said compressor and said exhaust passage.

* * * * *